June 28, 1955 M. E. DREYER Plant Pat. 1,401

PEAR TREE

Filed April 5, 1952 2 Sheets-Sheet 1

Inventor
Marie E. Dreyer
by Talbert Dick & Adler
Attorneys

PEAR TREE

Filed April 5, 1952 2 Sheets-Sheet 2

Inventor
Marie E. Dreyer
by Talbert Dick & Adler
Attorneys

United States Patent Office

Plant Pat. 1,401
Patented June 28, 1955

1,401

PEAR TREE

Marie E. Dreyer, Freeport, Ill.

Application April 5, 1952, Serial No. 280,778

1 Claim. (Cl. 47—62)

My invention relates to a new and distinct variety of pear tree.

The tree from which my new pear variety comes was originally purchased for a Bartlett pear tree. This tree was planted in the yard of my residence at 625 West Chestnut Street, Freeport, Illinois. After growth started on the newly planted tree, leaves and growth habit developed which were obviously different from those of the well known Bartlett pear. As further leaves and growth developed and the tree blossomed and produced fruit, its entire habit, methods of fruiting, and the fruit itself, proved to be entirely different from any pear known to be in existence.

Normally pear trees form fruiting buds in the summer and fall which bear the flowers and fruit the following year. These buds bloom all at the same time and set fruit that matures all about the same time. My new variety forms normal fruiting buds in early fall which blossom at the usual time in the spring and set a normal crop of pears.

The great difference between my variety and any other pear variety, however, is that, as the new growth is formed by the growing tree, new flower buds are formed on the new growth, and the flowering continues throughout the spring and into the summer. As a result of this continuous re-blooming there is a continuous succession of fruit formed throughout the spring and summer and consequently on the same branch there will be fruit in varying stages of growth from the tiny new fruit recently formed, to fruit approaching maturity, depending upon the date.

The fruit from the first blooming of my new pear will mature in late August in the same manner as other varieties of pears mature. But, because of the re-blooming or everbearing qualities of my new pear, mature fruit can be picked again at frequent intervals throughout September, and also into October until growth is checked by fall freezes. Even after freezing, there usually are some immature pears on the branches.

Another outstanding and distinguishable characteristic of my new pear variety is that it produces blossoms considerably smaller in size than those found normally on pear trees. The leaves are a characteristic rich dark green, and much smaller in size than average pear leaves. They also remain on the tree throughout the balance of the winter, even though frozen, in contrast to other varieties which drop their foliage after freezing weather occurs.

My new variety of pear tree has been asexually reproduced by grafting in the States of Illinois and Iowa and the results show that the characteristics hereinabove described have been established.

The fruit of this new variety is about average size for the ordinary garden pear and is of excellent quality with no signs of any gritty formation inside which destroys the eating qualities of many other varieties. It is a good eating pear, stores well and is very suitable for canning purposes.

Figure 1:
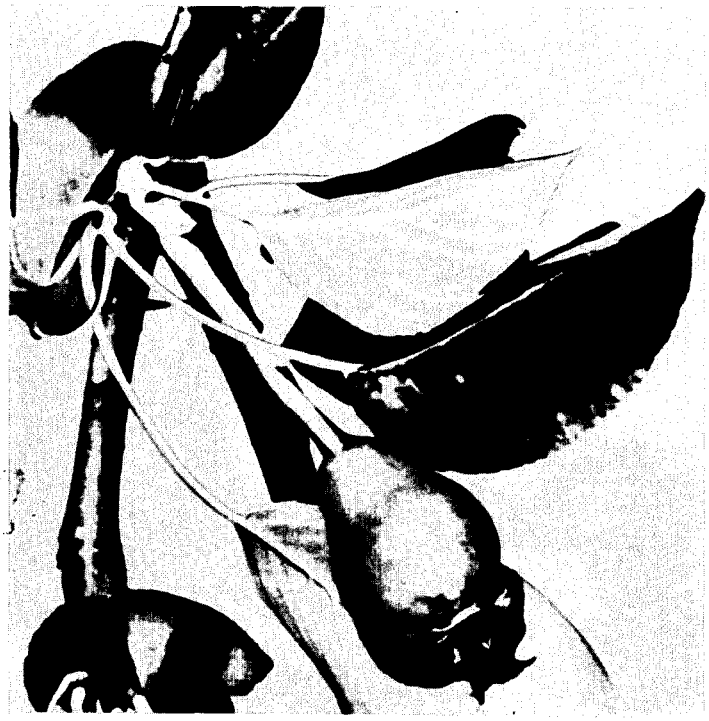
Figure 2:
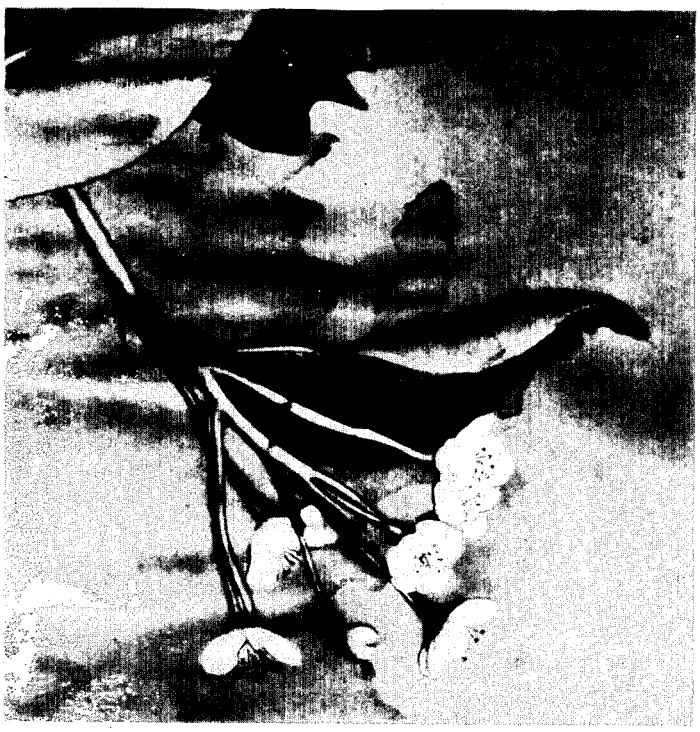
Figure 2:
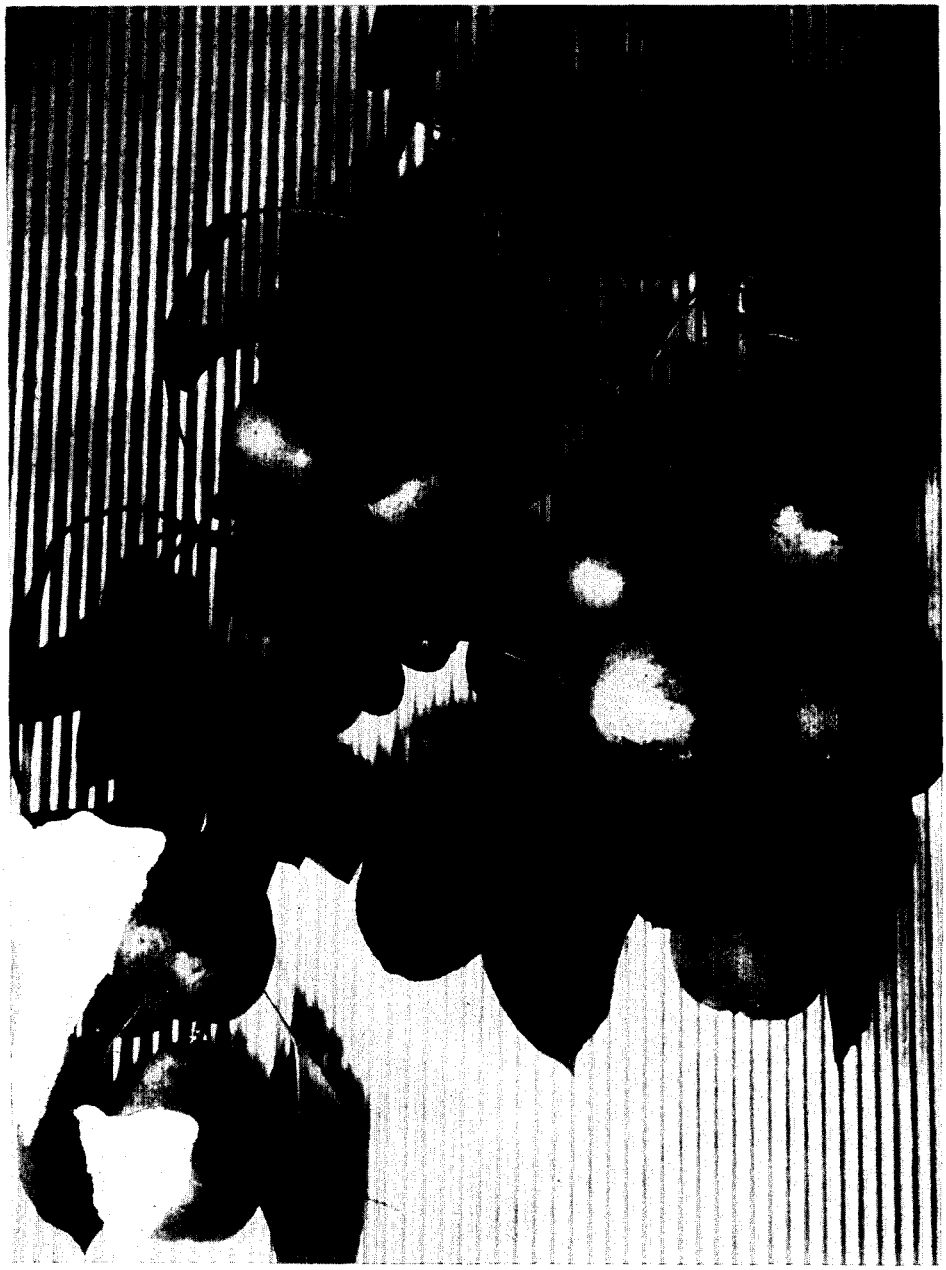

While the outstanding novel characteristics of this new variety of pear tree are of an intangible nature, the fruit and other characteristics thereof are shown in the accompanying drawing, in which Fig. 1 shows fruit on fruit spurs formed on old wood, Fig. 2 shows a different portion of the branch shown in Fig. 1 to illustrate the flowers at the terminal which are present at the same time as the fruit shown in Fig. 1 and Fig. 3 shows fruit in different stages of maturity on the same branches. This new variety is more particularly identified in the following detailed description.

Tree: Medium size. Upright growth. Very productive and bears every year in contrast to other varieties that bear only every other year.

*Height.*—From 20 to 25 feet.

*Trunk.*—Of average size—about 8 inches in diameter.

*Leaves.*—Dark glossy green. A much darker green than most leaves of pear varieties. Length—2–2¼ inches. Width—1¼–1½ inches. Grow singly. Ovate.

*Buds.*—White with pink tops before opening. Hardy.

*Flowers.*—Color—white. Usually bloom in early May. Small and are unusual in that they are about one-half the size as the flowers of other pear varieties being an inch or less in diameter.

*Roots.*—Spreading. Strong and hardy.

Fruit:

*Ripening period.*—About August 25th for the first crop of normal fruit from the early blossoms. Other fruit continue to ripen from that time until all growth is checked by freezing temperatures. The continuous blooming of this everbearing tree produces fruit in various varying stages of maturity, and therefore with widely different ripening dates on the same branch.

*Size and shape.*—About 2¾ inches long—2½ inches wide. Oblong—obovate—pyriform with unequal sides. Weight—5 to 6 ounces or over.

*Base or stems.*—Unusually long—1½ to 1¾ inches—rather slim. Basin 1½ inches.

*Skin.*—Color yellow with pink cheeks. Very tender as to eating quality. Smooth without blemishes.

*Flesh.*—Color white. Flavor spicy—texture, fine. No grainy particles. Firm and has a delightful fragrance. Eating quality superior to the well known Bartlett pear variety.

*Core.*—Large, closed, axile, with clasping core-lines.

*Apex or blossom end.*—Calyx tube short, wide, conical.

*Seeds.*—In the first fruits, seeds are of normal quantity, medium in size and length, wide, plump, acute. Late pickings show few or no seeds in the fruit, indicating that the blossoms are self-pollinating.

Resistance to:

*Disease.*—No fireblight has developed in any plantings thus far in either Illinois or Iowa.

*Cold.*—It has not been injured by cold weather in either Illinois or Iowa since origination.

*Wind.*—Branches hold up well and resist breaking even in high winds and loaded with fruit.

*Soil conditions.*—Plantings in clay soil, marshal silt and in the heavy "gumbo" in Iowa all are growing well.

Storage qualities: Very good. It has been noted that either when ripened on the tree, or ripened in storage, there is no tendency in this variety to develop a rot along the core in the center of the fruit, as is so common with many pear varieties.

Ease of asexual reproduction: Easily reproduced by grafting or budding, and this operation has been carried on both in Illinois and in Iowa.

Special or unique foliage: Leaves unusually small and noticeably darker green than most pear varieties. Leaves remain on the tree throughout most of the winter even though frozen, which is not a characteristic of ordinary pear varieties.

Everbearing qualities: Blooms in the normal manner compared with other pears, but as new wood is formed, new buds appear thereon, and the resulting blossoms mature into fruit. This blooming is continuous throughout the summer. Fruit from first buds mature normally in August and fruit from later buds continue to mature throughout September and into October until freezing weather.

Canning qualities: Good. Flavor has high spiciness which makes the canned fruit delicious.

Shipping qualities: Good.

I claim:

A new and distinct variety of pear tree characterized as to novelty by the continuous appearance in the same season of buds on the new wood as it forms, which buds blossom and bear fruit to give the tree everbearing qualities whereby fruit in varying stages of maturity is present on the same branch and mature at varying times relative to the formation of the buds, by its leaves maintaining a dark green color and being smaller than those of most pear varieties and remaining on the tree throughout the winter, and by the bearing of fruit each year of a delicious quality, substantially as described.

No references cited.